United States Patent [19]

Shiota et al.

[11] Patent Number: 5,856,453
[45] Date of Patent: Jan. 5, 1999

[54] GLYCOPHOSPHOLIPID

[75] Inventors: Makoto Shiota, Kawagoe; Goro Hanagata, Sayama; Kiyoshi Tatsumi, Iruma, all of Japan

[73] Assignee: Snow Brand Milk Products Co., Ltd., Japan

[21] Appl. No.: 440,904

[22] Filed: May 15, 1995

[30] Foreign Application Priority Data

May 17, 1994 [JP] Japan .................................. 6-128169
Jun. 15, 1994 [JP] Japan .................................. 6-155484

[51] Int. Cl.$^6$ .................................................. C07H 13/00
[52] U.S. Cl. ........................ 536/18.7; 536/17.2; 536/17.9
[58] Field of Search ................. 536/17.2, 17.9, 536/18.7

[56] References Cited

U.S. PATENT DOCUMENTS

| | | | |
|---|---|---|---|
| 4,310,505 | 1/1982 | Baldeschwieler et al. ................ | 424/1 |
| 4,480,041 | 10/1984 | Myles et al. ............................ | 436/508 |
| 4,762,822 | 8/1988 | Ettinger ................................. | 514/25 |
| 4,957,768 | 9/1990 | Dutilh .................................... | 426/604 |
| 5,183,680 | 2/1993 | Jodlbauer .............................. | 426/611 |

FOREIGN PATENT DOCUMENTS

| | | | |
|---|---|---|---|
| 0 493 622 A1 | 7/1992 | European Pat. Off. ........ | C08B 37/00 |
| 2 692 781 A1 | 12/1993 | France ............................. | A61K 7/02 |
| 42211890A1 | 1/1994 | Germany ....................... | C07H 13/04 |

OTHER PUBLICATIONS

J.D. Billimoria et al., "Synthesis of Phosphatidylethanolamine–N–Glucoside" *Chemistry and Industry* 1731–1732 (1968).

J.D. Billimoria et al., "The Phospholipids of Butter and Their Effect on Blood Coagulation" *Biochemical Journal* 78(1):185–194 (1961).

T. Mizuochi et al., "A Library of Oligosaccharide Probes (Neoglycolipids) from N–Glycosylated Proteins Reveals That Conglutinin Binds to Certain Complex–Type as Well as High Mannose–Type Oligosaccharide Chains" *Journal of Biological Chemistry* 264(23:13834–13839 (1989).

Y.S. Park et al., "Interaction of Synthetic Glycophospholipids with Phospholipid Bilayer Membranes" *Biochimica et Biophysica Acta* 1112:251–258 (1992).

Y.S. Park et al., "Cryoprotective Activity of Synthetic Glycophospholipids and Their Interactions with Trehalose" *Biochimica et Biophysica Acta* 1124:241–248 (1992).

C.A.A. Van Boeckel et al., "Phosphotriester Approach To The Synthesis of α–Glucosylated Mono– and Diphosphatidyl Glycerols: Bacterial Cell–Wall Components", Tetrahedron, vol. 37, No. 21, pp. 3751–3761 (1981).

J.J. Oltvoort et al., "A simple approach to the synthesis of a membrane teichoic acid fragment of Staphylococcus aureus", Recueil, Journal of the Royal Netherlands Chemical Society, 101/3, pp. 87–91 (1982).

C.A.A. Van Boeckel and J.H. Van Boom, "Synthesis of Glucosylphosphatidylglycerol Via A Phosphotriester Intermediate", Tetrahedron Letters, No. 37, pp. 3561–3564, (1979).

C.A.A. Van Boeckel and J.H. Van Boom, "Synthesis Of Phosphatidyl–α–Glucosyl–Diacylglycerol Containing Palmitic And Oleic Acid Esters", Tetrahedron Letters, No. 21, pp. 3705–3708, (1980).

*Primary Examiner*—Elli Peselev
*Attorney, Agent, or Firm*—Testa, Hurwitz & Thibeault, LLP

[57] ABSTRACT

The present invention relates to glycophospholipids represented by the general formula [I]:

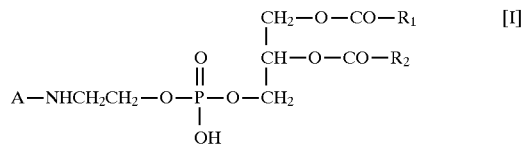

The glycophospholipid of the present invention can be obtained by extracting lipid fraction of whey, butter milk, etc. with a mixed solvent of chloroform/methanol and purifying by silica gel chromatography.

The glycophospholipid of the present invention is that having a novel structure and existing in milk lipid, and utilized as a biochemical reagent, a starting material for medicine and foodstuff or a surfactant.

6 Claims, 7 Drawing Sheets

GLYCOPHOSPHOLIPID

BACKGROUND OF THE INVENTION

1. Field of the Invention

The present invention relates to a novel glycophospholipid wherein glycerophospholipid links to a sugar molecule, and a process for preparation thereof. The glycophospholipid according to the present invention is useful as a biochemical reagent, a raw material for medicine and foodstuff, or a surfactant.

2. Background of the Invention

Phospholipids have various functions in organism. Phospholipids such as phosphatidylcholine, phosphatidylethanolamine, sphingomyelin, as a component of biomembrane, form bimolecular lipid membrane to protect cell membranes from external environment, thereby providing suitable environment for functioning of the protein. In addition, they are known to function as a resource of choline, phosphorus, fatty acids, and function as a depot of arachidonic acid for biosynthesis of prostaglandins. Recently, control mechanism of cell differentiation has been gradually revealed. Moreover, some phospholipids such as PAF (platelet activation factor) themselves demonstrate strong physiological activity. Accordingly, phospholipids have various important functions in organism.

Glycolipids are also ingredients of cell membrane. These glycolipids on the external surface of the cell membrane are considered to function as surface markers of cells because of the variety of sugar chain and of the different patterns of sugar chains expression according to the kind of cells. The differentiated cells express a specific glycolipid on a surface of the cell. The fact suggests that glycolipids have various cell functions. For example, function as a receptor, to control activity of membrane bound enzyme, to control ion channel, to control membrane fluidity, to control cell differentiation, etc.

Glycolipids are general name for materials containing both water-soluble sugar chain and fat-soluble group in a molecule. In animal cells, most of glycolipids are sphingolipids, containing sphingosine. Glyceroglycolipids, containing glycerol, are only found in vegetables, bacteria, etc. Recently, glyceroglycolipids have been considered to have some physiological activities in animal cells, for example, since seminolipid is found to exist in porcine testes. In connection with phospholipid and sugar, it is found that phosphatidylinositol functions as an anchor (GPI anchor) which links to protein through inositol binding sugar chain in a molecule to connect protein to cell membrane. Structural analysis of various GPI anchors such as those of Trypanosoma membrane antigen, human red cell acetylcholine esterase, etc. have been reported. The protein can move on a surface of a membrane, so GPI is considered to control the enzymatic activity and function as a receptor. Up to date, however, compounds wherein sugar links to glycerophospholipid have not been found. There are no report on existence of glycolipid in milk of mammal, for example in cow's milk.

The present inventors have found a material exhibiting color reaction characteristic to phospholipid and sugar by thin layer in isolated and purified fractions chromatography from milk, and have isolated a fraction of phospholipid by repeating purification and isolation according to compound lipid purification methods mainly including column chromatography. As a result of structural analysis of these fractions, It was confirmed for the first time that unknown glycophospholipid exist in milk.

Accordingly, the present invention relates to a novel glycophospholipid, particularly glycophospholipid wherein sugar links to glycerophospholipid, and intends to provide a process for preparing such glycophospholipid.

BRIEF DESCRIPTION OF DRAWINGS

FIG. 6 shows thin layer chromatograms of the glycophospholipid of the present invention at various steps of purification. In FIG. 6, Fr. means fraction, GPL means glycophospholipid of the present invention, SPM means sphingomyelin, PC means phosphatidylcholine, LacCer means lactosylceramide.

SUMMARY OF THE INVENTION

The object of the present invention is to provide glycophospholipid having the following physico-chemical properties (1) to (12):

(1) the following proton peaks detected by proton NMR: four proton peaks at approximately 4.0 ppm, a proton peak at 5.1 ppm, an anomeric proton peak at 4.2 ppm, a methyl proton peak at 0.9 ppm, and a proton peak at 1.5–3.0 ppm;

(2) characteristic absorption at 3,500 cm$^-$, 1,000 cm$^-$ and 1,300 cm$^-$ as determined by Fourier transformation infrared analysis;

(3) decomposed by phospholipase C;

(4) color reaction characteristic of phospholipid using Dittmer-Lester reagent;

(5) releasing sugar by β-galactosidase;

(6) color reaction characteristic of sugar using orcinol-sulfuric acid, diphenylamine-aniline reagent;

(7) comprising galactose as a constituent sugar;

(8) colored with ninhydrin;

(9) an ethanolamine moiety existing in a molecule according to the quantitative determination;

(10) a glycerol moiety existing in a molecule according to the quantitative determination;

(11) a molecule of phosphoric acid group existing in a molecule according to quantitative determination of phosphorous;

(12) $C_{12-20}$ saturated or unsaturated fatty acid is detected by analysis of methyl ester after decomposition with hydrochloric acid/methanol.

Another object of the present invention is to provide glycophospholipid of the following general formula (I):

(wherein $R_1$ and $R_2$ denote the same or different saturated or unsaturated aliphatic hydrocarbon residue, A denotes a sugar with N-glycosidic linkage).

Still another object of the present invention is to provide a process for preparation of the above glycophospholipid from milk or milk product as a starting material.

DETAILED DESCRIPTION OF THE INVENTION AND PREFERRED EMBODIMENTS

The glycophospholipid of the present invention can be extracted and purified from milk or milk product. As milk products, lipid fraction obtained from cheese whey, butter milk, etc. can be used. For example, as shown in Examples, protein of cheese whey, powdered cheese whey, butter milk, etc. are decomposed by protease, successively added with methanol, chloroform, then stirred to extract compound lipid. The glycophospholipid can be prepared by extracting such lipid fractions with a mixture of chloroform/methanol or a mixture of chloroform/methanol/water, followed by silica-gel chromatography, the adsorbed fraction being eluted with a solvent such as chloroform/methanol, chloroform/methanol/acetic acid/water as a mobile phase, then collecting fractions showing glycophospholipid reaction. Thus obtained glycophospholipid occurs as a composition of several glycophospholipids usually with different aliphatic hydrocarbons. The glycophospholipid of the present invention can be obtained in such forms. Alternatively, the product may be further purified. The glycophospholipid of the present invention is represented by the following general formula (I):

(wherein $R_1$ and $R_2$ are the same or different saturated or unsaturated aliphatic hydrocarbon residue, A denotes sugar with N-glycosidic linkage).

Particularly, in the formula, $R_1$ and $R_2$ are the same or different $C_{13-17}$ saturated or unsaturated, straight-chain aliphatic hydrocarbon group, for example, at least one selected from the group consisting of tridecanyl ($C_{13:0}$), pentadecanyl ($C_{15:0}$), pentadecenyl ($C_{15:1}$) heptadecanyl (C17:0), heptadecenyl ($C_{17:1}$) and heptadecedienyl ($C_{17:2}$), and, for example, A comprises, for example two galactose residues coupled with each other.

The physicochemical properties of the glycophospholipid of the present invention will be further explained in detail.

(1) Proton NMR Analysis

Figure 1:
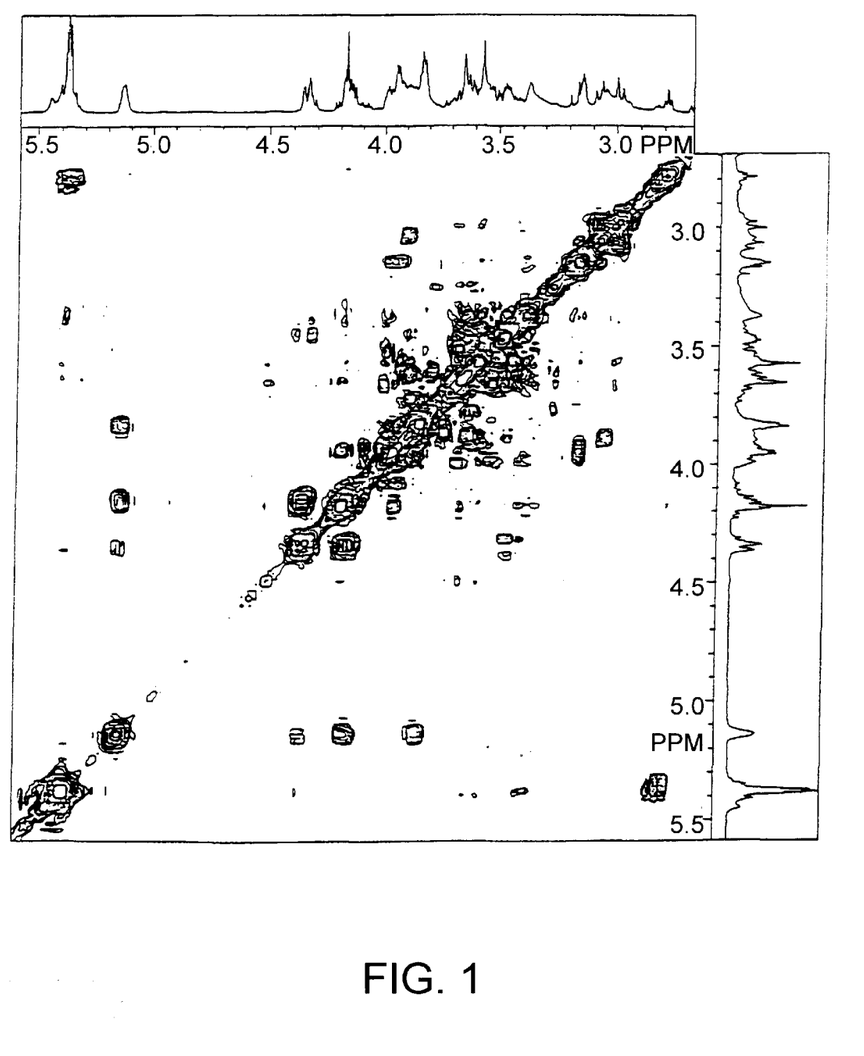
FIG. 1 shows two-dimensional NMR spectrum of the glycophospholipid of the present invention.
Figure 2:
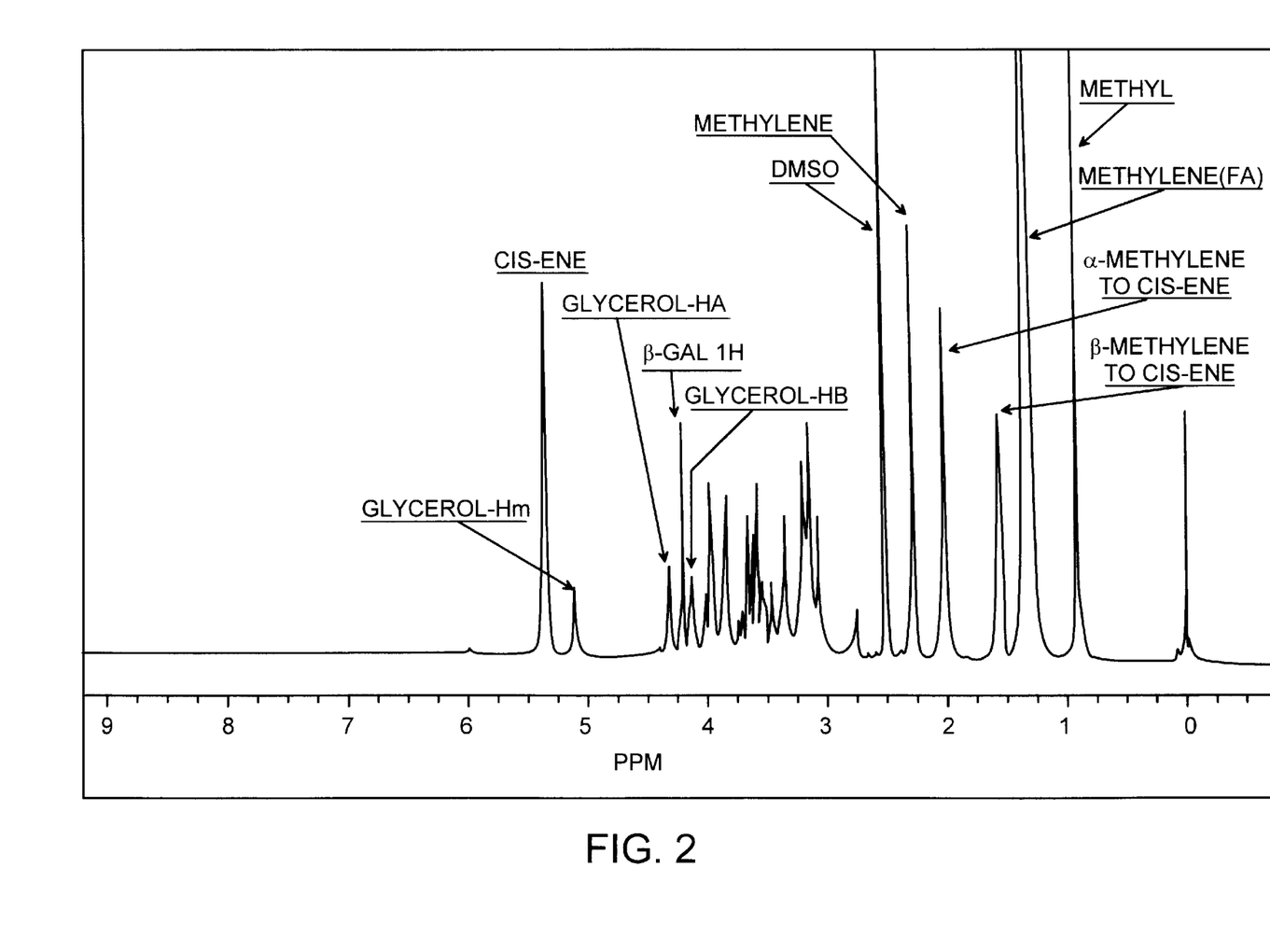
FIG. 2 shows NMR spectrum of the glycophospholipid of the present invention.

According to the known methods, the present glycophospholipid was dissolved in hexadeuterodimethyl sulfoxide-heavy water (98:2) and proton-proton two-dimensional NMR was determined. The spectrum is shown in FIG. 1. As the results, the material was identified as glycerolipid by four proton peaks at approximately 4.0 ppm, a chemical shift of a proton peak at 5.1 ppm which is characteristic of glycerol and correlation in two-dimensional NMR. The anomeric proton observed at 4.2 ppm and the coupling constant suggest existence of one sugar linking through β-linkage. The existence of proton derived from cis double bonded hydrogen at 5.4 ppm, methyl proton at 0.9 ppm and protons at 1.5–3.0 ppm are characteristic of fatty acid. One dimensional NMR is shown in FIG. 2.

(2) Reactivity with Phospholipase C

The glycophospholipid of the present invention is decomposed with phospholipase C (PLC). The glycophospholipid is proved to be glycerophospholipid because it is decomposed with PLC. The color reaction with Dittmer-Lester reagent, a phospholipid detecting reagent, yielded blue color which is characteristic of phospholipid.

(3) FT-IR Analysis

Figure 3:
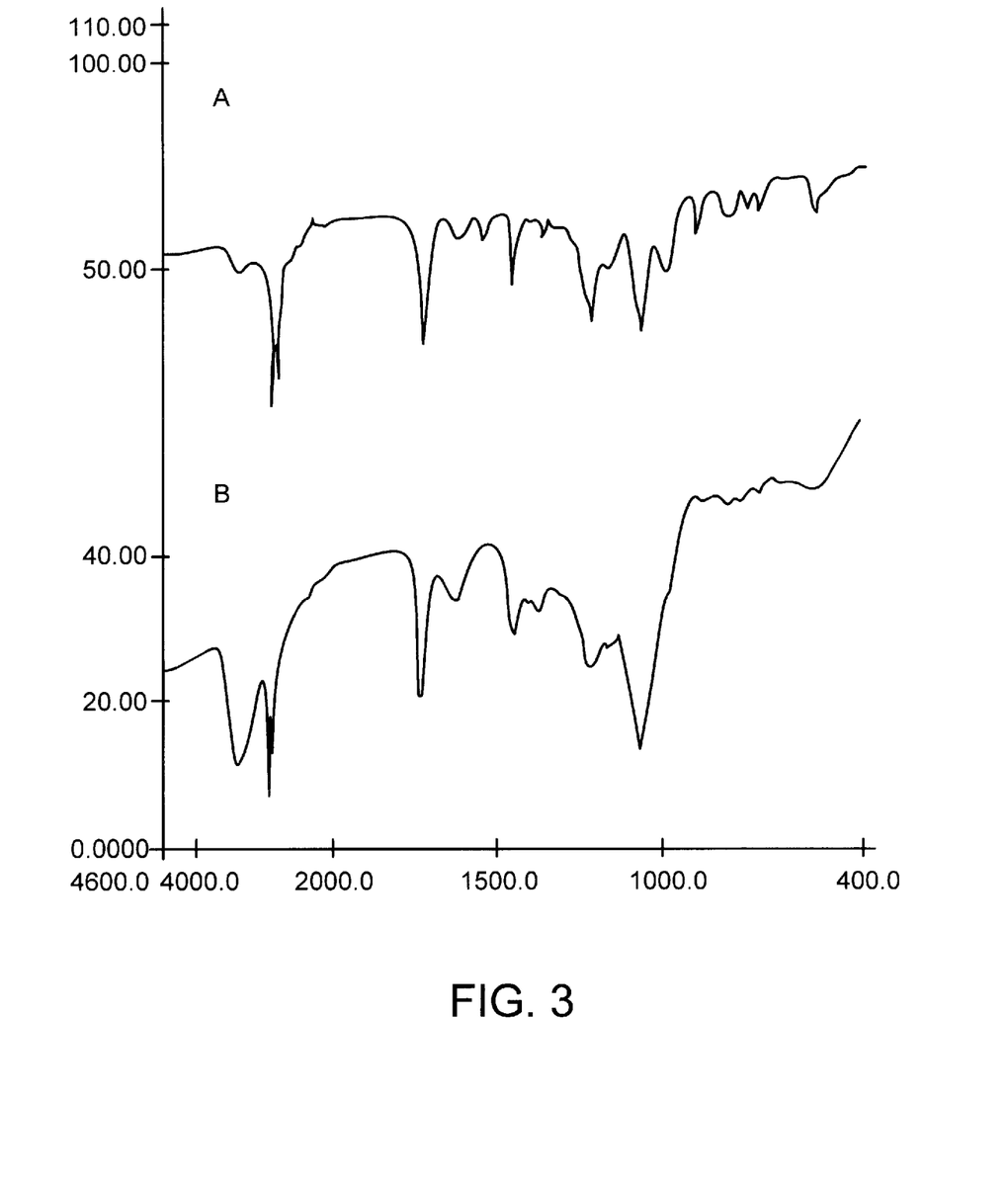
FIG. 3 shows absorption spectra of glycophospholipid of the present invention according to Fourier transformation infrared analysis (FT-IR). In the figure, A and B are absorption spectra of the standard phosphatidylethanolamine and glycophospholipid of the present invention, respectively.

Analysis according to Fourier transformation infrared analysis (FT-IR) observed adsorption at 3,500 $cm^{-1}$ derived from hydroxyl group, characteristic of sugar and 1,000 $cm^{-1}$ and 1,300 $cm^{-1}$ derived from phosphoric acid were observed. In addition, weak and broad absorption derived from non-binding hydroxyl group of phosphoric acid at 2,500–2,800 $cm^{-1}$ were observed. Accordingly, the glycophospholipid of the present invention was confirmed not to occur as triester but to have diester structure of phosphoric acid in the molecule. The FT-IR absorption pattern of the glycophospholipid of the present invention and that of phosphatidylethanolamine (PE) measured as a control are shown in FIG. 3. As shown in the figure, the pattern of the present glycophospholipid is almost identical to the absorption pattern of the standard PE. However, absorption at 1,560 $cm^{-1}$, which is characteristic of a primary amine and found in PE spectra, was not observed in the present compound. No absorption of amide was observed. Accordingly, it is supposed that the sugar has N-glycosidic linkage.

(4) Sugar Analysis

The glycophospholipid of the present invention was colored with orcinol-sulfuric acid, diphenylamine-aniline reagent which specifically react with sugar.

Further, the product treated with 6N HCl at 100° C. for 3 hours was converted to trimethylsilyl (TMS) derivative, and subjected to GC/MS analysis. The qualitative analysis by thin layer chromatography (TLC) of the product decomposed with 0.2N sulfuric acid, decomposed with 2N trifluoroacetic acid (TFA) and treated at 100° C. was conducted. The product was converted to alditol acetate by treatment with 0.3N sulfuric acid/90% acetic acid at 80° C. for 14 hours, then GC/MS analysis of the sugar was performed. Using HPLC equipped the pulsed amperometric detecterie qualititative analysis of the product treated with 1N TFA at 100° C. for 1.5 hours was performed. All results of the analysis suggested the existence of galactose.

According to the aforementioned analysis, it is confirmed that all the constituent sugars are galactose.

(5) Reaction with Glycosidase

Sequential decomposition of the glycophospholipid was tried with various glycosidase. As the result, the sugar is released only with β-galactosidase. The above results, together with the above NMR data, showed the existence of β-linkage of galactose. One residue of galactose was released by glycosidase treatment for a molecule of the glycophospholipid of the present invention. The following analysis showed that two residues of galactose exist as linking to each other. However, one of galactose residues is not released by glycosidase. Therefore, it is confirmed that the galactose residue does not link through O-glycosidic linkage to phospholipid.

(6) FAB (Fast Atom Bombardment)—MS Analysis

Figure 4A:
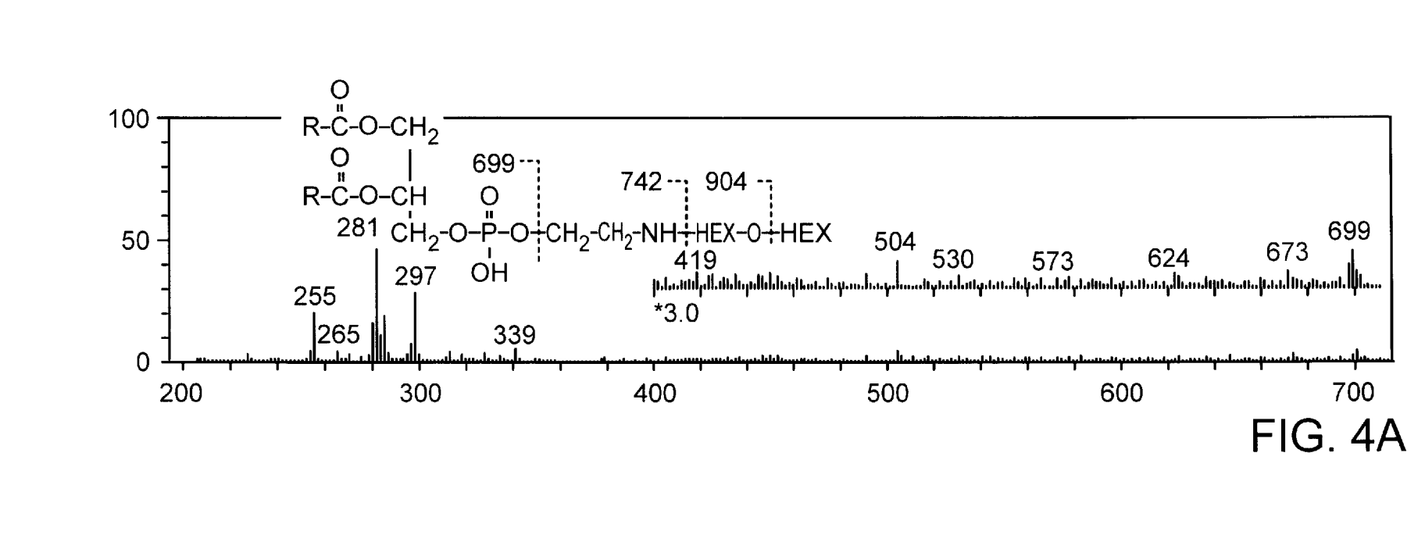
FIG. 4 shows FAB-MS spectra of the glycophospholipid of the present invention. M denotes a representative molecular weight of the glycophospholipid of the present invention. In the figure, $[\text{M-162-162-H}]^-$ means a fragment of a material with the elimination of two saccharides, and $[\text{M-162-H}]^-$ means a spectrum of a material with the elimination of one saccharide, and $[\text{M—H}]^-$ means a spectrum [TM1] of a material with the elimination of one hydrogen.
Figure 4B:
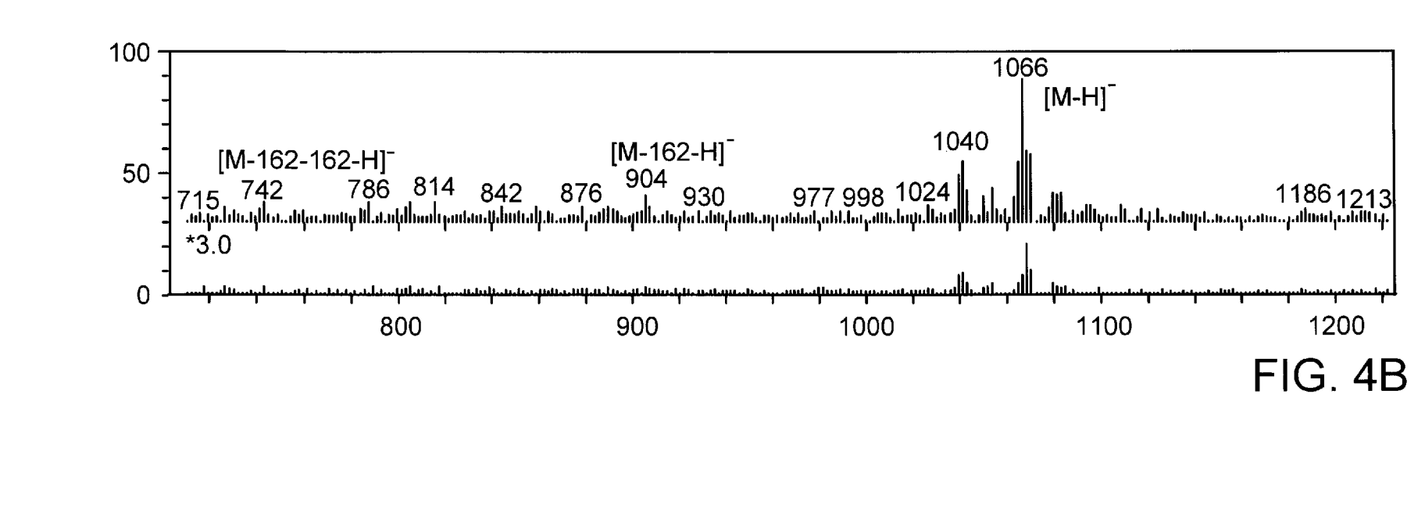

The glycophospholipid of the present invention was assessed by anion FAB-MS using triethanolamine as a matrix. As the result, a moiety composed of two residues having molecular weight of 180, which is considered to be a sugar, is confirmed to exist in the glycophospholipid molecule. The moiety was identified to be two galactoses linked according to its sugar composition. One type of the glycophospholipid of the present invention was confirmed to have molecular weight of 1067. The FAB-Mass Spectrum is shown in FIG. 4.

(7) Confirmation of the Linkage Site of Galactose

Figure 5A:
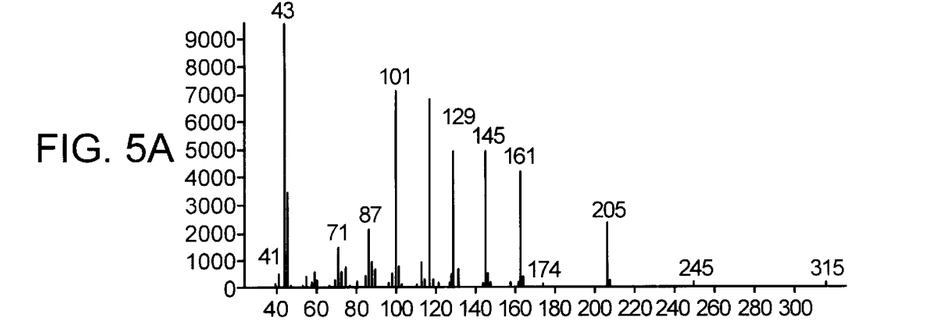
FIG. 5 shows GC-MS spectra of the glycophospholipid of the present invention. In the figure, the upper column of (a) shows mass spectrum of the separated material of GC retention time of 17.949 min. and the lower column shows mass spectrum of 1,5-diacetyl-2,3,4,6-tetra-O-methylhexitol. In the figure, the upper column of (b) is mass spectra of the separated material of GC retention time of 23.361 min. and the lower column is mass spectrum of 1,5,6-tri-O-acetyl-2,3,4-tri-O-methylhexitol.
Figure 5B:
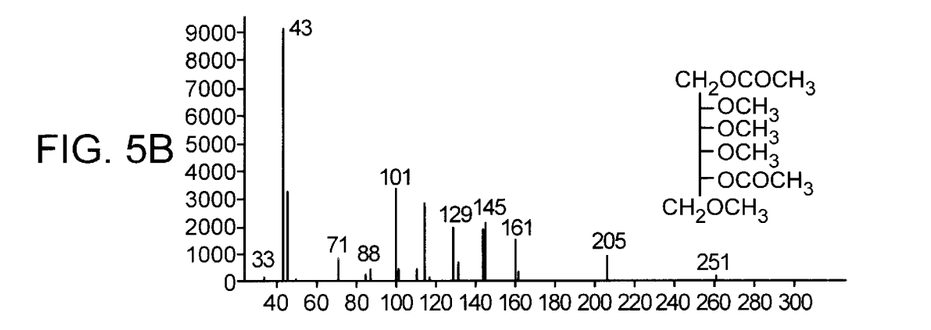
Figure 5C:
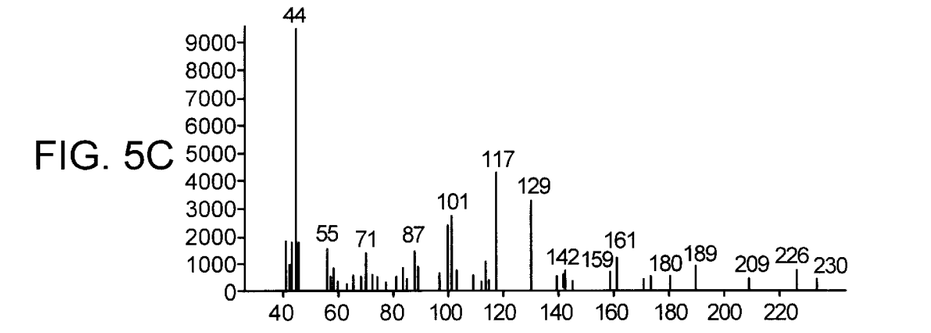
Figure 5D:
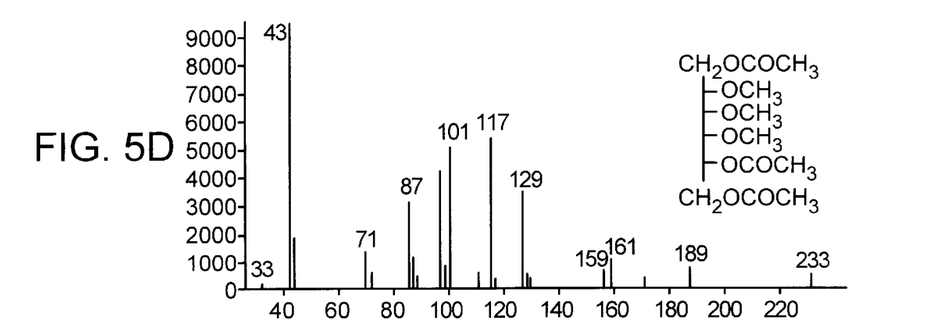

To determine the linkage site of the said sugar, methylation analysis was performed. Using Hakomori's method, the sugar was completely methylated, hydrolyzed with 0.5N sulfuric acid/90% acetic acid to release methylated sugar. The free methylated sugars were reduced, converted to alditols, and the free hydroxyl groups were acetylated with acetic anhydride. The GC/MS analysis of the resulting partially methylated alditol acetates was performed, and the results are shown in FIG. 5. The standard of the acetyl derivative of the partially methylated hexitol was submitted to GC-MS analysis under the same conditions for identification. According to the mass spectrum, 1,5-diacetyl-2,3,4,6-tetra-O-methylhexitol was observed (RT 17.949 min.) (FIG. 5-a). 1,5,6,7-tri-O-acetyl-2,3,4-tri-O-methylhexitol was observed (RT 23.361 min.)(FIG. 5-b). According to the above results, the glycophospholipid of the present invention has two galactose molecules linked through β1,6 linkage.

(8) Ethanolamine Analysis and Confirmation of Phosphatidylethanolamine Skeleton

The glycophospholipid of the present invention is colored with ninhydrin. Further, TLC, GC analysis of TMS derivative suggest that strong acid decomposition with 6N hydrochloric acid produces ethanolamine.

After strong acid decomposition, according to colorimetry with dinitrofluorobenzene, the amount of ethanolamine present in the glycophospholipid was determined. As the results, an ethanolamine was found to be present in a molecule of glycophospholipid.

On the other hand, the glycophospholipid of the present invention was hydrolyzed with 0.2N sulfuric acid, or 0.1N hydrochloric acid at 100° C. and TLC analysis of the hydrolysate was performed. A spot with Rf same as that of phosphatidylethanolamine (PE) was detected, in those of the some hydrolysates of the glycophospholipid of the present invention. This spot was positive to Dittmer-Lester color reaction, positive to ninhydrin color reaction and negative to orcinol-sulfuric acid color reaction. As the result, this spot was confirmed to be derived from phosphatidylethanolamine. The above results confirmed that the glycophospholipid of the present invention have phosphatidylethanolamine skeleton.

(9) Glycerol Analysis

The glycophospholipid of the present invention, after decomposed with 2N hydrochloric acid at 125° C. for 48 hours, was reacted with sodium periodate, and the produced formaldehyde was reacted with chromotropic acid and colorimetry of the resulting reddish purple material was performed. As the result, the glycophospholipid was confirmed to have one glycerol per a molecule.

(10) Phosphorous analysis

The glycophospholipid of the present invention, after decomposed with 10N hydrochloric acid at 180° C. for 3 hours, was reacted with ammonium molybdate, and the produced ammonium molybdophosphate was quantitatively determined. Thus, one phosphoric acid group was confirmed to exist in one molecule of the glycophospholipid.

(11) Fatty Acid Analysis

The glycophospholipids of the present invention contain fatty acids in their structure. Decomposition with 5% hydrochloric acid/methanol followed by gas chromatography of the produced fatty acid methyl ester confirmed that the glycophospholipids have fatty acids of the following constitution. The relative constitution ratio of the fatty acid shown below is an example. The ratio varies depending on the source of the glycophospholipid of the present invention, but most of them are $C_{12-20}$ saturated or unsaturated straight chain fatty acids.

TABLE 1

| Constitution fatty acid | % |
|---|---|
| C14:0 | 1.6 |
| C16:0 | 14.4 |
| C16:1 | 1.9 |
| C18:0 | 17.1 |
| C18:1 | 52.7 |
| C18:2 | 12.0 |

The phospholipid of the following formula [II] is shown as a representative structure with the above characteristics.

The glycophospholipid of the present invention has structure wherein sugar links to glycerophospholipid. The glycophospholipid possesses the aforementioned physiological functions. Further, the linkage between phospholipid and sugar may afford the phospholipid functions which no conventional phospholipids have. The glycophospholipid may function as a GPI anchor or a precursor thereof according to their structural similarity.

Further, the phospholipid comprises a hydrophilic moiety, mainly consisting of phosphoric acid group, and a hydrophobic moiety such as fatty acid and the long-chain base of sphingolipid in a molecule. The glycophospholipid can be used for foodstuff as a emulsifier because of such amphipathic property and natural origin. The glycophospholipid of the present invention has extremely high hydrophilic property as phospholipid and is effectively dispersed in water because it has sugar in its structure. Further, because the glycophospholipid of the present invention is glycerophospholipid, substitution and removal of the fatty acid moiety can be relatively easily performed. Accordingly, when the glycophospholipid of the present invention is used as an emulsifier, the HLB value can be readily altered. The purified, synthetic product and composition of the glycophospholipid can be utilized as a useful material as an emulsifier, particularly O/W emulsifier.

According to the characteristics as an surfactant, the glycophospholipid can be applied to the field of medicine, foodstuff as well as cosmetics.

As mentioned above, the present invention provides a novel glycophospholipid which is expected to be applied in the various field, for example, a biochemical reagent, a starting material for medicine and foodstuff or as a surfactant.

The process for preparation of the glycophospholipid of the present invention will be illustrated in detail in the following examples.

[EXAMPLE 1]

This example illustrates a process for recovering glycophospholipid of the present invention from cheese whey containing phospholipid.

Powdered cheese whey (3 kg) was dissolved in a warm water (30 L) and kept at 50° C. *Bacillus subtilis* protease (10 g) was added and the reaction was carried out at pH 8, 45° C. for 15 hours. After protein was decomposed, the reaction mixture was heated at 90° C. for 10 minutes to deactivate the enzyme. Methanol (80 L) was added and the reaction mixture was stirred at room temperature for 30 minutes. Further, chloroform (40 L) was added and stirred for 30 minutes and a compound lipid was extracted. The extract was then filtered, concentrated to dryness. Subsequently, a mixture of chloroform/methanol (2:1,v/v, 500 mL) was added and stirred at room temperature for 30 minutes, and filtered. Acetone (20 L) was added to the filtrate and allowed to stand at 4° C. overnight to give a white precipitate (112 g). The precipitate was dissolved in a small amount of chloroform/methanol mixture and chromatographed on a silica gel column (stepwise elution using mobile phase: chloroform/methanol/water 90:10:0, 80:20:2, 70:30:3, 60:40:4, by vol.).

Figure 6A:
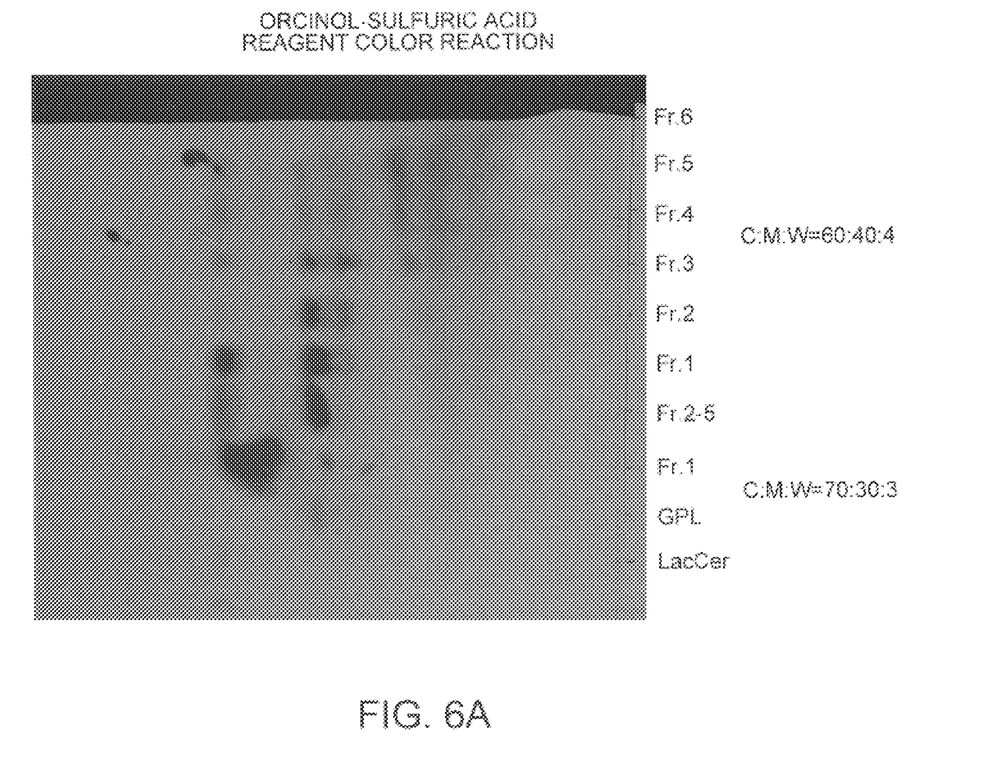
Figure 6B:
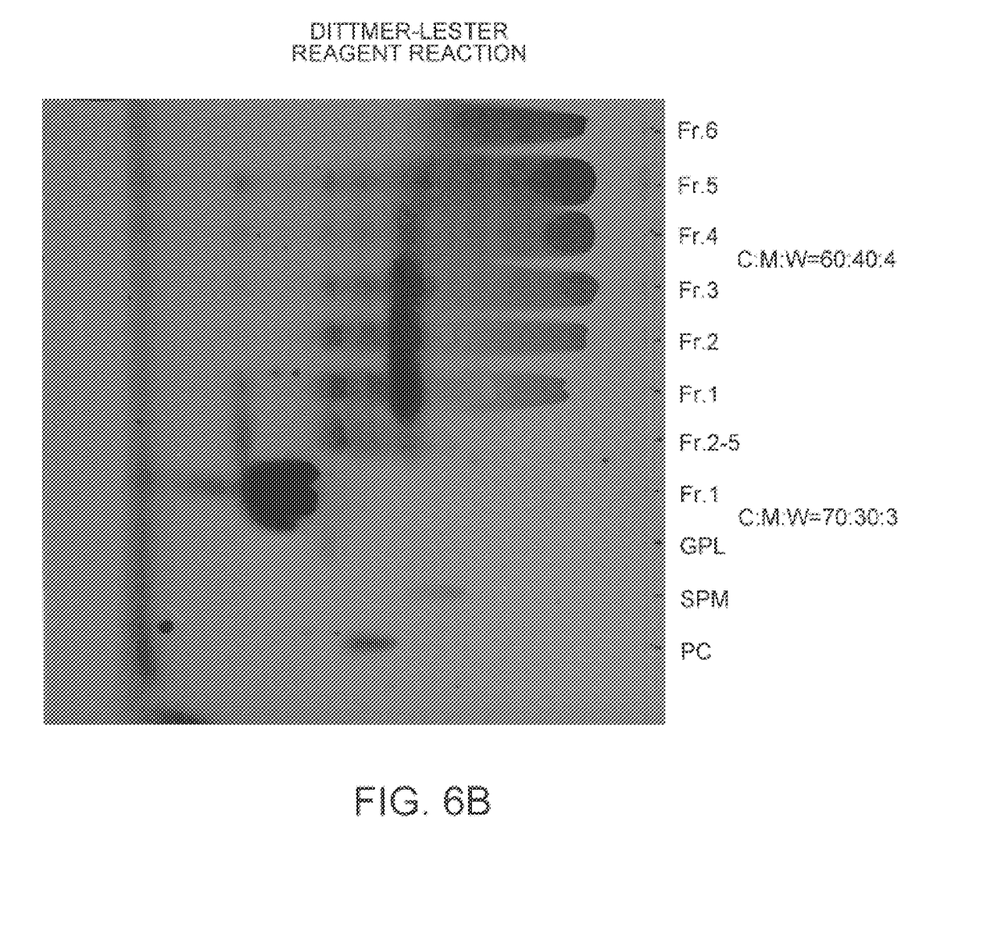

The TLC at each purification stages is shown in FIG. 6.

The glycophospholipid was developed by TLC, and the spots colored with both orcinol-sulfuric acid reagent and Dittmer-Lester reagent were identified as glycophospholipid. Such stepwise elution yielded a fraction containing 16.24 g of glycophospholipid. Subsequently, silica gel column chromatography was carried out using a mixed solvent (chloroform/methanol/acetone/acetic acid/water 10:2:4:2:1) as mobile phase. At this purification stage, 3.20 g of glycophospholipid of about 90% purity (determined by color reaction with orcinol-sulfuric acid reagent and Dittmer-Lester reagent) was obtained. The purified product was subjected to TLC development followed by ninhydrin color reaction. As the result, ninhydrin coloring matter existed which was considered to be a hydrophobic peptide component. The purified product was dissolved in a mixed solvent (chloroform/methanol 1:1). The ninhydrin coloring matter was removed by gel filtration using Sephadex LH-20 to obtain 2.28 g of glycophospholipid. Then, the resultant product was subjected to a silica gel column chromatography (mobile phase: chloroform/methanol/acetic acid/water (65:25:8:4) and chloroform/methanol/water (65:35:8)) to give 1.54 g of glycophospholipid (98% purity). This material possessed characteristics of glycophospholipid described above.

[EXAMPLE 2]

This example illustrates a process for preparation from powder containing high concentration of compound lipid from milk.

According to a method disclosed in Japanese Patent Laying-Open No. 292880/1993, powder containing high concentration of complex lipid was prepared. That is, butter milk was acidified to give isoelectric precipitate. After the precipitate was removed, ultra filtration concentration was conducted, and the resulting solution was dried to prepare powder containing high concentration of compound lipid.

This powder (100 g) was suspended in acetone (1 L), and the resulting suspension was vigorously stirred to disperse the powder. Then the mixture was left at 4° C. overnight. The precipitate was collected by filtration, then lyophilized to give 33 g of white powder. One gram aliquot was suspended in ethanol. The resultant ethanol insoluble material was filtered off, which was dissolved in hexane/ethanol/acetic acid/water=60/40/5/5 (5 mL), and chromatographed on a silica gel column using the same mixed solvent as a mobile phase (three 80×500 mm column combined; resin, spherical silica gel (SIL-120-S-50, YMC; UV detection at 205 nm). Each peak detected was identified using the color reaction Dittmer-Lester reagent and orcinol-sulfuric acid reagent. These peaks were well resolved and glycophospholipid existed as a single peak. A fraction containing glycophospholipid was recovered and lyophilized to give 85 mg of white powder. According to phosphorus analysis, the content of phospholipid was 81%. The content of glycophospholipid in the phospholipid was 92%.

What is claimed is:

1. A purified glycophospholipid isolated from milk or milk a product comprising the following physico-chemical properties (1) to (12):

(1) has the following proton peaks detected by proton NMR: four proton peaks at approximately 4.0 ppm, a proton peak at 5.1 ppm, an anomeric proton peak at 4.2 ppm, a methyl proton peak at 0.9 ppm and a proton peak at 1.5–3.0 ppm;

(2) has characteristic absorption at about 3,500 cm$^{-1}$, 1,000 cm$^{-1}$ and 1,300 cm$^{-1}$ as determined by Fourier transformation infrared analysis;

(3) decomposes when treated with phospholipase C;

(4) displays a color reaction characteristic of phospholipid when contacted with Dittmer-Lester reagent;

(5) releases sugar when contacted with β-galactosidase;

(6) displays a color reaction characteristic of sugar when contacted with orcinol-sulfuric acid, diphenylamine-aniline reagent;

(7) has two sugar molecules linked via a β(1→6) linkage, wherein the end terminal sugar is galactose;

(8) is colored when treated with ninhydrin;

(9) has an ethanolamine moiety according to quantitative analytical determination of nitrogen, carbon and hydrogen;

(10) has a glycerol moiety according to quantitative analytical determination of carbon and hydrogen;

(11) has a phosphoric acid group according to quantitative analytical determination of phosphorous; and (12) has a $C_{12-20}$ saturated or unsaturated fatty acid which can be detected by analysis of methyl ester after decomposition when contacted with hydrochloric acid/methanol.

2. A glycophospholipid according to claim 1 having the following formula (I):

wherein $R_1$ and $R_2$ each represents a saturated or unsaturated aliphatic hydrocarbon residue comprising from about twelve to about twenty carbon atoms, and A comprises a sugar moiety having an N-glycosidic linkage wherein said moiety contains two sugar molecules linked via a β(→6) linkage wherein the terminal sugar is β-galactose.

3. A glycophospholipid according to claim 2, wherein each of $R_1$ and $R_2$ is selected from the group consisting of tridecanyl ($C_{13:0}$), pentadecanyl ($C_{15:0}$), heptadecanyl ($C_{17:0}$), pentadecenyl ($C_{15:1}$), heptadecenyl ($C_{17:1}$) and heptadecedienyl ($C_{17:2}$).

4. A glycophospholipid according to claim 2 or 3, wherein A is a dimer of galactose.

5. A glycophospholipid according to claim 2 represented by the following formula (II):

6. A purified glycophospholipid comprising the following physico-chemical properties (1) to (12):

(1) has the following proton peaks detected by proton NMR: four proton peaks at approximately 4.0 ppm, a proton peak at 5.1 ppm, an anomeric proton peak at 4.2 ppm, a methyl proton peak at 0.9 ppm and a proton peak at 1.5–3.0 ppm;

(2) has characteristic absorption at about 3,500 $cm^{-1}$, 1,000 $cm^{-1}$ and 1,300 $cm^{-1}$ as determined by Fourier transformation infrared analysis;

(3) decomposes when treated with phospholipase C;

(4) displays a color reaction characteristic of phospholipid when contacted with Dittmer-Lester reagent;

(5) releases sugar when contacted with β-galactosidase;

(6) displays a color reaction characteristic of sugar when contacted with orcinol-sulfuric acid, diphenylamine-aniline reagent;

(7) has two molecules of galactose linked together via a β(1→6) linkage;

(8) is colored when treated with ninhydrin;

(9) has an ethanolamine moiety according to quantitative analytical determination of nitrogen, carbon and hydrogen;

(10) has a glycerol moiety according to quantitative analytical determination of carbon and hydrogen;

(11) has a phosphoric acid group according to quantitative analytical determination of phosphorous; and (12) has a $C_{12-20}$ saturated or unsaturated fatty acid which can be detected by analysis of methyl ester after decomposition when contacted with hydrochloric acid/methanol.

* * * * *